US012576085B2

(12) United States Patent
Sawyer et al.

(10) Patent No.: US 12,576,085 B2
(45) Date of Patent: Mar. 17, 2026

(54) COMBINATION COMPRISING AN ATP ANALOG AND AN ADENOSINE RECEPTOR ANTAGONIST OR A NUCLEOBASE/NUCLEOSIDE ANALOG FOR THE TREATMENT OF CANCER

(71) Applicants: Michael Bruce Sawyer, Edmonton (CA); Vijayalakshmi Damaraju, Edmonton (CA)

(72) Inventors: Michael Bruce Sawyer, Edmonton (CA); Vijayalakshmi Damaraju, Edmonton (CA)

( * ) Notice: Subject to any disclaimer, the term of this patent is extended or adjusted under 35 U.S.C. 154(b) by 0 days.

(21) Appl. No.: 15/426,798

(22) Filed: Feb. 7, 2017

(65) Prior Publication Data

US 2017/0143725 A1 May 25, 2017

Related U.S. Application Data

(62) Division of application No. 13/881,918, filed as application No. PCT/CA2011/001177 on Oct. 26, 2011, now abandoned.

(60) Provisional application No. 61/406,856, filed on Oct. 26, 2010.

(51) Int. Cl.
| | |
|---|---|
| A61K 31/522 | (2006.01) |
| A61K 31/404 | (2006.01) |
| A61K 31/513 | (2006.01) |
| A61K 31/517 | (2006.01) |
| A61K 31/5377 | (2006.01) |
| A61K 31/635 | (2006.01) |
| A61K 45/06 | (2006.01) |

(52) U.S. Cl.
CPC .......... *A61K 31/522* (2013.01); *A61K 31/404* (2013.01); *A61K 31/513* (2013.01); *A61K 31/517* (2013.01); *A61K 31/5377* (2013.01); *A61K 31/635* (2013.01); *A61K 45/06* (2013.01)

(58) Field of Classification Search
CPC .. A61K 31/522; A61K 31/404; A61K 31/513; A61K 31/517; A61K 31/5377; A61K 31/635; A61K 45/06; A61K 2300/00
See application file for complete search history.

(56) References Cited

U.S. PATENT DOCUMENTS

| | | | | |
|---|---|---|---|---|
| 2003/0139428 A1* | 7/2003 | Kalla | .................. | C07D 473/00 514/263.2 |
| 2012/0052005 A1* | 3/2012 | Ding | .................... | C07D 473/12 424/1.11 |

OTHER PUBLICATIONS

Guidance for Industry and Reviewers (U.S. Department of Health and Human Services, Nov. 18, 2002, https://www.fda.gov/OHRMS/DOCKETS/98fr/02d-0492-gdl0001-vol1.pdf).*
Ye et al. (Endocrine Reviews, 31, 578-599; Aug. 2010) (Year: 2010).*
Baraldi et al. (Chem. Rev., 108, 238-263, 2008) (Year: 2008).*
Loriot, Nature Clinical Practice Oncology May 2008, vol. 5 No. 5 (Year: 2008).*
Tally, Surgery 1996;120:248-54 (Year: 1996).*
Ward, The Journal of Biological Chemistry vol. 275, No. 12, Issue of Mar. 24, pp. 8375-8381, 2000. (Year: 2000).*
Te et al. ("Southern Medical Journal", Dec. 1, 1989, 82(12):1497-1500). (Year: 1989).*
Edes et al., *Nosocomial Diarrhea: Beware the Medicinal Elixir*, South Med. J., Abstract only, 82(12):1497-1500, 1989.*
Baraldi et al., "Adenosine Receptor Antagonists: Translating Medicinal Chemistry and Pharmacology into Clinical Utility", *Chemical Reviews*, vol. 108(1); pp. 238-263 (2008).
Barnes, Peter J., "Future Treatments of Chronic Obstructive Pulmonary Disease and Its Comorbidities", *Proceedings of the American Thoracic Society*, vol. 5, 8 pages (2008).
Bruns et al. "Adenosine receptor binding; Structure-activity analysis generates extremely potent xanthine antagonists", *Proc. Natl. Acad. Sci USA*, vol. 80, 4 pages (Apr. 1983).
Culpitt et al, "Effects of Theophylline on Induced Sputum Inflammatory Indices and Neutrophil Chemotaxis in Chronic Obstructive Pulmonary Disease", *American Journal of Respiratory and Critical Care Medicine*, vol. 165, 6 pages (2002).
Gridelli et al. "Erlotinib in Non-Small Cell Lung Cancer Treatment: Current Status and Future Development", *The Oncologist*, 12, pp. 840-849 (2007).
Lentini et al., "Anti-Invasive Effects of Theophylline on Experimental B16-F10 Melanoma Lung Metastasis", *Cancer Journal*, vol. 10(5); 274-278 (1997).
Mass of an Adult; edited by Glenn Elert, "The Physics Factbook", accessed on Aug. 19, 2016 at http://hypertextbook.com/facts/2003/AlexSchlessingerman.shtml (2003).
Notification Concerning Transmittal of International Preliminary Report on Patentability (Chapter I of the Patent Cooperation Treaty) in corresponding PCT Application No. PCT/CA2011/001177 mailed May 10, 2013 (10 pages).
Notification of Transmittal of the International Search Report and the Written Opinion of the International Searching Authority, or the Declaration in corresponding PCT Application No. PCT/CA2011/001177 mailed Jan. 20, 2012 (14 pages).
Ye et al., "The Evolving Field of Tyrosine Kinase Inhibitors in the Treatment of Endocrine Tumors", *Endocrine Reviews*, vol. 31(4), 578-599 (Aug. 2010).
O'Mahony F et al. Induction of Na+/K+/2Cl− cotransporter expression mediates chronic potentiation of intestinal epithelial Cl-secretion by EGF. Am J Physiol. Apr. 2008; 294: C1362-C1370.
Aherne et al. "Epithelial-specific A2B adenosine receptor signaling protects the colonic epithelial barrier during acute colitis" Nature, 8(6):1324-1338 (2015).
Bowen "Mechanisms of TKI-induced diarrhea in cancer patients" Supportive and Palliative Care, 7(2):162-167 (2013).

(Continued)

*Primary Examiner* — Jean P Cornet
(74) *Attorney, Agent, or Firm* — Reichel Stohry Dean LLP; Natalie J. Dean

(57) ABSTRACT
A method for treating an ATP analog-induced side effect in a subject comprises administering an effective amount of an adenosine receptor antagonist to the subject. A method for treating cancer in a subject comprises administering a nucleobase and/or nucleoside prior to administering an ATP analog.

17 Claims, 12 Drawing Sheets

(56) References Cited

OTHER PUBLICATIONS

Hirsh et al. "Management of diarrhea induced by epidermal growth factor receptor tyrosine kinase inhibitors" Current Oncology, 21(6):329-336 (2014).

Liu et al. "Assessment and management of diarrhea following VEGF receptor TKI treatment in patients with ovarian cancer" Gynecologic Oncology, 150:173-179 (2018).

Schiller "Antidiarrheal Drug Therapy" Current Gastroenterology Reports, 19:18 (2017).

Secombe et al. "Diarrhea Induced by Small Molecule Tyrosine Kinase Inhibitors Compared With Chemotherapy: Potential Role of the Microbiome" Cancer and the Microbiome, 19:1-12 (2020).

Abraham et al. "Drug-induced Diarrhea" Current Gastroenterology Reports, 9:365-372 (2007).

* cited by examiner

COMBINATION COMPRISING AN ATP ANALOG AND AN ADENOSINE RECEPTOR ANTAGONIST OR A NUCLEOBASE/NUCLEOSIDE ANALOG FOR THE TREATMENT OF CANCER

FIELD OF THE INVENTION

This invention relates to cancer treatment. More specifically, this invention relates to combination treatments for cancer.

BACKGROUND OF THE INVENTION

Throughout this application, various references are cited to describe more fully the state of the art to which this invention pertains. The disclosures of these references are hereby incorporated by reference into the present disclosure in their entirety.

A major advance of decades of investigating carcinogenesis and metastasis has been targeted treatment development. Tyrosine kinases are popular targets for cancer treatment and include CD20, Her-2/neu, and epidermal growth factor receptors. Antibodies and small molecule inhibitors have been designed in order to inhibit these targets.

Many small molecule tyrosine kinase inhibitors (TKIs) are known, including vandetanib, sunitinib, and erlotinib. TKIs act by binding to the ATP binding pocket of tyrosine kinases, thereby preventing their phosphorylation and signaling cascade. These were designed to specifically inhibit tyrosine kinases, however, off-target effects are known to occur in some cases. Off-target effects of other protein inhibitors, such as mTOR inhibitors, Bcl-2 inhibitors, and PARP inhibitors are also known to occur.

For example, 30% of patients treated with erlotinib develop diarrhea. The diarrhea is currently managed by reducing the dose of the TKI or by treatment with loperamide. To date, a satisfactory explanation for TKI-induced diarrhea has not been provided. An additional side effect includes hand-foot syndrome, which is also not well explained.

Nucleoside analogs are taken up into cells through nucleoside transporters. Nucleoside analogs are often used in cancer treatment and include agents such as gemcitabine and capecitabine. Many clinical studies have tried combining nucleoside analogs with TKIs for improved cancer treatment and most of these studies have failed. The reasons for clinical failure have been poorly understood.

Nucleobase analogs, such as 5-fluorouracil (5-FU), are also commonly used in cancer treatment. Little is known about the transport mechanisms of nucleobases into and out of cells; however, Damaraju et al. (Biochemical Pharmacology, 2008, 75, 1901-1911) characterized a sodium-independent nucleobase transport activity.

Chemotherapy regimens involving 5-FU (nucleobase analog) and capecitabine (nucleoside analog) are called FOLFOX (5-FU and oxaliplatin), FOLFIRI (5-FU and irinotecan), and XELOX (capecitabine and oxaliplatin). In each of these regimens, TKIs, if used, are administered on the same day or days as the other chemotherapeutic agents.

The above limitations in conventional chemotherapy can result in problematic side effects and, consequently, dose reductions. Additionally, there may be off-target effects of TKIs and other protein inhibitors that confound the findings of clinical trials that attempt to combine TKIs, or other protein inhibitors, with conventional chemotherapeutic agents. As will be appreciated, improvements in treatments involving the use of TKIs are desired.

SUMMARY OF THE INVENTION

In an aspect, there is provided a method for treating and/or preventing an ATP analog-induced side effect in a subject, the method comprising administering an effective amount of an adenosine receptor antagonist to the subject.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the side effect is diarrhea and/or hand-foot syndrome. In another aspect, the side effect is diarrhea and the method reduces the incidence or severity of the diarrhea.

In another aspect, there is provided a method for treating and/or preventing cancer in a subject, the method comprising administering an ATP analog and an adenosine receptor antagonist to the subject.

In another aspect, the method is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the adenosine receptor antagonist treats and/or prevents an ATP analog-induced side effect. In another aspect, the side effect is diarrhea and/or hand-foot syndrome. In another aspect, the side effect is diarrhea and the method reduces the incidence or severity of the diarrhea.

In accordance with another aspect, there is provided a method for maintaining or escalating dose intensity of an ATP analog in a subject, the method comprising administering the ATP analog together with an adenosine receptor antagonist.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In a further aspect, the adenosine receptor antagonist treats and/or prevents an ATP analog-induced side effect. In another aspect, the side effect is diarrhea and/or hand-foot syndrome. In another aspect, the side effect is diarrhea and the method reduces the incidence or severity of the diarrhea.

In accordance with another aspect, there is provided a combination treatment comprising an ATP analog and an adenosine receptor antagonist, wherein the adenosine receptor antagonist treats and/or prevents a side effect induced by the ATP analog.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the adenosine receptor antagonist treats and/or prevents an ATP analog-induced side effect. In another aspect, the side effect is diarrhea and/or hand-foot syndrome. In another aspect, the side effect is diarrhea and the method reduces the incidence or severity of the diarrhea.

In accordance with another aspect, there is provided a method for treating and/or preventing cancer in a subject, the method comprising administering a nucleobase and/or nucleoside analog prior to administering an ATP analog.

In another aspect, the method is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the method comprises administering the nucleobase analog prior to administering the ATP analog. In another aspect, the nucleobase analog comprises at least one of 5-fluorouracil, allopurinol, azathioprine, mercaptopurine, and thioguanine. In another aspect, the nucleobase analog comprises 5-fluorouracil.

In another aspect, the nucleobase and/or nucleoside analog and the ATP analog act synergistically to treat and/or prevent cancer in the subject. In another aspect, the nucleobase and/or nucleoside analog and the ATP analog act additively to treat and/or prevent cancer in the subject.

In another aspect, the nucleobase and/or nucleoside analog is administered before the ATP analog.

In another aspect, the method further comprises administering an adenosine receptor antagonist to the subject. In another aspect, the adenosine receptor antagonist is administered concurrently with the ATP analog. In another aspect, the adenosine receptor antagonist comprises at least one methylxanthine. In another aspect, the at least one methylxanthine comprises at least one of caffeine, theophylline, and aminophylline.

In accordance with another aspect, there is provided a method of treating and/or preventing cancer in subject, the method comprising administering:

an ATP analog and a nucleoside or nucleobase analog to a subject in a combined amount that is effective to treat and/or prevent the cancer; and an adenosine receptor antagonist in an amount effective to treat and/or prevent an ATP analog-induced side effect in the subject.

In another aspect, the method is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the nucleobase analog comprises at least one of 5-fluorouracil, allopurinol, azathioprine, mercaptopurine, and thioguanine. In another aspect, the nucleobase analog comprises 5-fluorouracil.

In another aspect, the nucleobase and/or nucleoside analog and the ATP analog act synergistically to treat and/or prevent cancer in the subject. In another aspect, the nucleobase and/or nucleoside analog and the ATP analog act additively to treat and/or prevent cancer in the subject.

In another aspect, the adenosine receptor antagonist is administered concurrently with the ATP analog In another aspect, the adenosine receptor antagonist comprises at least one methylxanthine. In another aspect, the at least one methylxanthine comprises at least one of caffeine, theophylline, and aminophylline.

In accordance with another aspect, there is provided a use of an effective amount of an adenosine receptor antagonist for the manufacture of a medicament for treating and/or preventing an ATP analog-induced side effect in a subject.

In accordance with another aspect, there is provided a use of an effective amount of an adenosine receptor antagonist for treating and/or preventing an ATP analog-induced side effect in a subject.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the side effect is diarrhea and/or hand-foot syndrome. In another aspect, the side effect is diarrhea and the use reduces the incidence or severity of the diarrhea.

In accordance with another aspect, there is provided a use of an ATP analog and an adenosine receptor antagonist for the manufacture of a medicament for treating and/or preventing cancer in a subject.

In accordance with another aspect, there is provided a use of an ATP analog and an adenosine receptor antagonist for treating and/or preventing cancer in a subject.

In another aspect, the use is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the adenosine receptor antagonist treats and/or prevents an ATP analog-induced side effect. In another aspect, the side effect is diarrhea and/or hand-foot syndrome. In another aspect, the side effect is diarrhea and the use reduces the incidence or severity of the diarrhea.

In accordance with another aspect, there is provided a use of an ATP analog and an adenosine receptor antagonist for the manufacture of a medicament for maintaining or escalating dose intensity of the ATP analog in a subject.

In accordance with another aspect, there is provided a use of an ATP analog together with an adenosine receptor antagonist for maintaining or escalating dose intensity of the ATP analog in a subject.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the ATP analog and the adenosine receptor antagonist are administered simultaneously or sequentially. In another aspect, the ATP analog is administered before the adenosine receptor antagonist. In another aspect, the adenosine receptor antagonist is administered before the ATP analog.

In another aspect, the adenosine receptor antagonist treats and/or prevents an ATP analog-induced side effect. In another aspect, the side effect is diarrhea and/or hand-foot syndrome. In another aspect, the side effect is diarrhea and the use reduces the incidence or severity of the diarrhea.

In accordance with another aspect, there is provided a use of a nucleobase and/or nucleoside analog and an ATP analog for the manufacture of a medicament for treating and/or preventing cancer in a subject, wherein the nucleobase and/or nucleoside analog is formulated for administration prior to the ATP analog.

In accordance with another aspect, there is provided a use of a nucleobase and/or nucleoside analog prior to an ATP analog for treating and/or preventing cancer in a subject.

In another aspect, the use is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the nucleobase analog comprises at least one of 5-fluorouracil, allopurinol, azathioprine, mercaptopurine, and thioguanine. In another aspect, the nucleobase analog comprises 5-fluorouracil.

In another aspect, the nucleobase and/or nucleoside analog and the ATP analog act synergistically to treat and/or prevent cancer in the subject. In another aspect, the nucleobase and/or nucleoside analog and the ATP analog act additively to treat and/or prevent cancer in the subject.

In another aspect, the use further comprises administering an adenosine receptor antagonist to the subject.

In another aspect, the adenosine receptor antagonist is administered concurrently with the ATP analog.

In another aspect, the adenosine receptor antagonist comprises at least one methylxanthine. In another aspect, the at least one methylxanthine comprises at least one of caffeine, theophylline, and aminophylline.

In accordance with another aspect, there is provided a use of an ATP analog, a nucleoside or nucleobase analog, and an adenosine receptor antagonist in the manufacture of a medicament for treating cancer in a subject, wherein the ATP analog and the nucleoside or nucleobase analog are for use in a combined amount that is effective to treat and/or prevent the cancer; and the adenosine receptor antagonist is for use in an amount effective to treat and/or prevent an ATP analog-induced side effect in the subject.

In accordance with another aspect, there is provided a use of an ATP analog and a nucleoside or nucleobase analog in a combined amount that is effective to treat and/or prevent cancer in a subject; and an adenosine receptor antagonist in an amount effective to treat and/or prevent an ATP analog-induced side effect in the subject.

In another aspect, the use is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the nucleobase analog comprises at least one of 5-fluorouracil, allopurinol, azathioprine, mercaptopurine, and thioguanine. In another aspect, the nucleobase analog comprises 5-fluorouracil.

In another aspect, the nucleobase and/or nucleoside analog and the ATP analog act synergistically to treat and/or prevent cancer in the subject. In another aspect, the nucleobase and/or nucleoside analog and the ATP analog act additively to treat and/or prevent cancer in the subject.

In another aspect, the adenosine receptor antagonist is administered concurrently with the ATP analog.

In another aspect, the adenosine receptor antagonist comprises at least one methylxanthine. In another aspect, the at least one methylxanthine comprises at least one of caffeine, theophylline, and aminophylline.

In accordance with another aspect, there is provided a composition comprising an ATP analog and an adenosine receptor antagonist, wherein the adenosine receptor antagonist treats and/or prevents a side effect induced by the ATP analog.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the adenosine receptor antagonist is non-specific. In another aspect, the adenosine receptor antagonist is specific for one or more adenosine receptors. In another aspect, the adenosine receptor antagonist is specific for an adenosine $A_2$ receptor. In another aspect, the adenosine receptor antagonist is specific for the adenosine $A_{2B}$ receptor. In another aspect, the adenosine receptor antagonist comprises at least one methylxanthine. In another aspect, the at least one methylxanthine comprises at least one of caffeine, theophylline, and aminophylline.

In another aspect, the adenosine receptor antagonist reduces an ATP analog-induced side effect. In another aspect, the side effect is diarrhea and/or hand-foot syndrome. In another aspect, the side effect is diarrhea and the composition reduces the incidence or severity of the diarrhea.

In accordance with another aspect, there is provided a kit for treating and/or preventing cancer in a subject, the kit comprising a nucleobase and/or nucleoside analog and an ATP analog, wherein the nucleobase and/or nucleoside analog is for administration prior to the ATP analog.

In another aspect, the kit is for treating cancer.

In another aspect, the ATP analog is selected from a tyrosine kinase inhibitor, an mTOR inhibitor, a Bcl-2 inhibitor, and a PARP inhibitor. In another aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In another aspect, the tyrosine kinase inhibitor comprises gefitinib. In another aspect, the Bcl-2 inhibitor comprises ABT 263.

In another aspect, the kit comprises a nucleobase analog. In another aspect, the nucleobase analog comprises at least one of 5-fluorouracil, allopurinol, azathioprine, mercaptopurine, and thioguanine. In another aspect, the nucleobase analog comprises 5-fluorouracil.

In another aspect, the nucleobase and/or nucleoside analog and the ATP analog act synergistically to treat and/or prevent cancer in the subject. In another aspect, the nucleobase and/or nucleoside analog and the ATP analog act additively to treat and/or prevent cancer in the subject.

In another aspect, the kit further comprises an adenosine receptor antagonist.

In another aspect, the adenosine receptor antagonist is for administration concurrently with the ATP analog.

In another aspect, the adenosine receptor antagonist comprises at least one methylxanthine. In another aspect, the at least one methylxanthine comprises at least one of caffeine, theophylline, and aminophylline.

In accordance with another aspect, there is provided a kit for treating and/or preventing cancer in a subject, the kit comprising an ATP analog and an adenosine receptor antagonist, wherein the adenosine receptor antagonist treats and/or prevents a side effect induced by the ATP analog.

In an aspect, the kit is for treating cancer.

In another aspect, the ATP analog is selected from a tyrosine kinase inhibitor, an mTOR inhibitor, a Bcl-2 inhibitor, and a PARP inhibitor. In an aspect, the PARP inhibitor comprises at least one of olaparib, ABT 888, and BSI-221. In another aspect, the tyrosine kinase inhibitor comprises at least one of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. In an aspect, the tyrosine kinase inhibitor comprises gefitinib.

In another aspect, the adenosine receptor antagonist is non-specific. In an aspect, the adenosine receptor antagonist is specific for one or more adenosine receptors. In an aspect, the adenosine receptor antagonist is specific for an adenosine $A_2$ receptor. In another aspect, the adenosine receptor antagonist is specific for the adenosine $A_{2B}$ receptor. In an aspect, the adenosine receptor antagonist comprises at least one methylxanthine. In an aspect, the at least one methylxanthine comprises at least one of caffeine, theophylline, and aminophylline.

In another aspect, the adenosine receptor antagonist reduces an ATP analog-induced side effect. In an aspect, the side effect is diarrhea and/or hand-foot syndrome. In an aspect, the side effect is diarrhea and the composition reduces the incidence or severity of the diarrhea.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Certain embodiments will now be described, by way of example only, with reference to the attached figures, wherein.

DETAILED DESCRIPTION OF THE EMBODIMENTS

Figure 1:
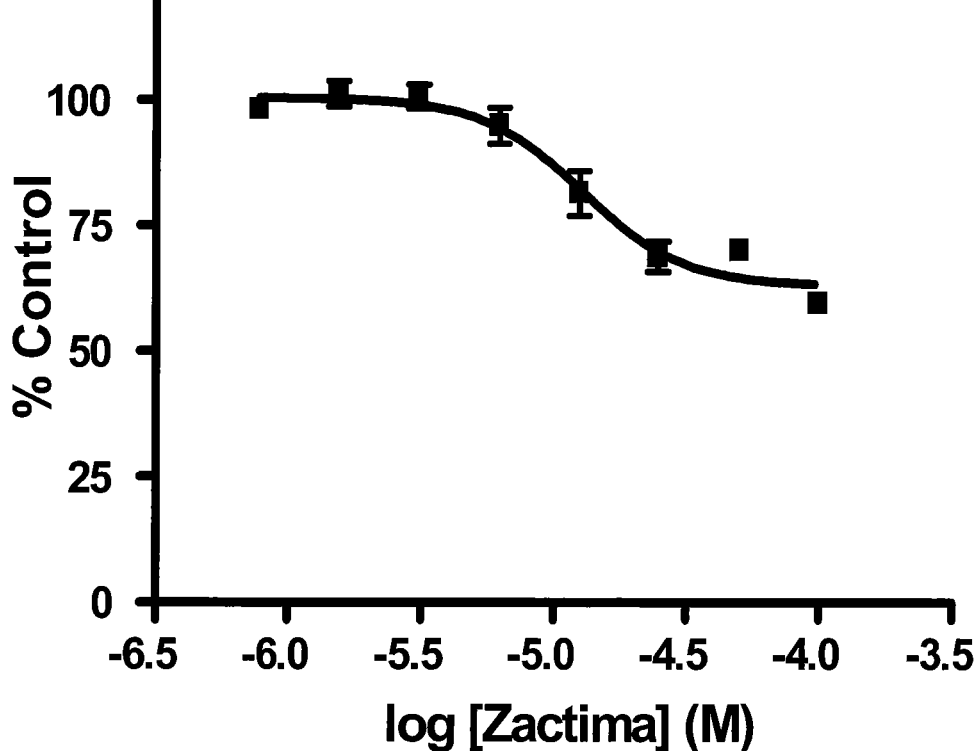
FIG. 1 is a dose response curve showing the inhibition of 1 μM [³H]adenine transport in human renal proximal tubule epithelial cells by vandetanib (Zactima™), averaged across three experiments.

The present invention encompasses methods and compositions for preventing and/or treating cancer and treatment-related side effects using ATP analogs such as, protein kinase inhibitors, for example, tyrosine kinase inhibitors (TKIs) in combination with adenosine receptor antagonists and/or nucleoside or nucleobase analogs.

Definitions

As used herein, an "ATP analog" is any anti-cancer compound that mimics the structure and/or function of ATP. Such anti-cancer compounds may act as ATP analogs as their primary function and/or this activity may be an "off-target" or secondary effect. Examples of ATP analogs include certain tyrosine kinase inhibitors, mammalian target of rapamycin (mTOR) inhibitors, B cell lymphoma (Bcl-2) inhibitors, and poly (ADP-ribose) polymerase (PARP) inhibitors. Tyrosine kinase inhibitors that are ATP analogs include, for example, axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, and vatalanib. Examples of mTOR inhibitors that are ATP analogs include rapamycin and its derivatives, sirolimus, temsirolimus, everolimus, zotarolimus and deforolimus. An example of a Bcl-2 inhibitor that is an ATP analog is ABT 263. Examples of PARP inhibitors that are ATP analogs include olaparib, ABT 888, and BSI-201. In another aspect, the present invention may specifically exclude one or more of these ATP analogs. In another aspect, the present invention may specifically exclude imatinib. Typically, ATP analogs cause side effects such as diarrhea and/or hand-foot syndrome.

As used herein, a "nucleoside analog" is any compound that mimics a nucleoside and may be incorporated into DNA and/or RNA, thereby disrupting or inhibiting replication, transcription, and/or translation. Non-limiting examples include 5-azacytidine, 5-aza2'-deoxycytidine, capecitabine, cladribine, cytarabine, deoxycoformycin, fludarabine, gemcitabine, and ribavirin. In another aspect, the present invention may specifically exclude one or more of these nucleoside analogs. In another aspect, the present invention may specifically exclude gemcitabine.

A "nucleoside transporter" is a compound that transports nucleosides into and out of a cell. Human nucleoside transporters include human equilibrative nucleoside transporter 1 (hENT1), human equilibrative nucleoside transporter 2 (hENT2), human equilibrative nucleoside transporter 3 (hENT3), human equilibrative nucleoside transporter 4 (hENT4), human concentrative nucleoside transporter 1 (hCNT1), human concentrative nucleoside transporter 2 (hCNT2), and human concentrative nucleoside transporter 3 (hCNT3).

As used herein, a "nucleobase analog" is any compound that mimics a nucleobase and may be incorporated into DNA and/or RNA, thereby disrupting or inhibiting replication, transcription, and/or translation. Non-limiting examples include 5-fluorouracil, allopurinol, azathioprine, mercaptopurine, and thioguanine.

A "nucleobase transporter" is a compound that transports nucleobases into and out of a cell. hENT2 and hENT3 are known to efficiently transport nucleobases and a sodium-independent transport mechanism for nucleobases has been described.

As used herein, an "adenosine receptor antagonist" is any compound that inhibits the activity of an adenosine receptor. Adenosine receptor antagonists may be, for example, antibodies, small molecule inhibitors, or proteins or peptides that block receptor function. Adenosine receptor antagonists may be specific or non-specific and include classic antagonists and partial agonists. Adenosine receptor antagonists may target any adenosine receptor or any combination of adenosine receptors, including the $A_1$, $A_2$, and/or $A_3$ adenosine receptors. In another aspect, the adenosine receptor antagonists may target the $A_{2A}$ and/or $A_{2B}$ adenosine receptors. Non-limiting examples of adenosine receptor antagonists include methylxanthines, such as caffeine, theophylline, and aminophylline.

As used herein, the term "cancer" refers to any malignant and/or metastatic disease. Examples of cancers include Acute Lymphoblastic Leukemia, Acute Myeloid Leukemia, Adrenocortical Carcinoma, AIDS-Related Cancers and Lymphomas, Anal Cancer, Appendix Cancer, Astrocytomas, Atypical Teratoid/Rhabdoid Tumor, Basal Cell Carcinoma, Bile Duct Cancer, Bladder Cancer, Bone Cancer, Brain Stem Glioma, Brain Tumor, Breast Cancer, Bronchial Tumors, Burkitt Lymphoma, Carcinoid Tumor, Carcinoma of Unknown Primary, Central Nervous System Atypical Teratoid/Rhabdoid Tumor, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Craniopharyngioma, Cutaneous T-Cell Lymphoma, Embryonal Tumors, Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer, Intraocular Melanoma, Eye Cancer, Gallbladder Cancer, Gastric (Stomach) Cancer, Gastrointestinal Carcinoid Tumor, Gastrointestinal Stromal Tumor (GIST), Gestational Trophoblastic Tumor, Glioma, Hairy Cell Leukemia, Head and Neck Cancer, Heart Cancer, Hepatocellular (Liver) Cancer, Hodgkin Lymphoma, Hypopharyngeal Cancer, Intraocular Melanoma, Islet Cell Tumors, Kaposi Sarcoma, Kidney (Renal Cell) Cancer, Langerhans Cell Histiocytosis, Laryngeal Cancer, Lip and Oral Cavity Cancer, Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myeloma, Nasal Cavity and Paranasal Sinus Cancer, Nasopharyngeal Cancer, Neuroblastoma, Non-Hodgkin Lymphoma, Non-Small Cell Lung Cancer, Oral Cancer, Oropharyngeal Cancer, Ovarian Cancer, Ovarian Epithelial Cancer, Ovarian Germ Cell Tumor, Ovarian Low Malignant Potential Tumor, Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Plasma Cell Neoplasm, Pleuropulmonary Blastoma, Primary Central Nervous System (CNS) Lymphoma, Prostate Cancer, Rectal Cancer, Respiratory Tract Cancer with Chromosome 15 Changes, Retinoblastoma, Rhabdomyosarcoma, Salivary Gland Cancer, Sézary Syndrome, Skin Cancer, Small Cell Lung Cancer, Small Intestine Cancer, Soft Tissue Sarcoma, Squamous Cell Carcinoma, Supratentorial Primitive Neuroectodermal Tumors, Testicular Cancer, Throat Cancer, Thymoma and Thymic Carcinoma, Thyroid Cancer, Thyroid Cancer, Transitional Cell Cancer of the Renal Pelvis and Ureter, Urethral Cancer, Uterine Cancer, Uterine Sarcoma, Vaginal Cancer, Vulvar Cancer, Waldenström Macroglobulinemia, and Wilms Tumor.

As used herein, the terms "treat", "treating", and "treatment" mean that a disease, disorder, or condition such as cancer, or a side effect such as, for example, diarrhea or hand-foot syndrome, is ameliorated, reduced, lessened, and/or alleviated. With specific reference to cancer treatment, these terms mean that the cancer may be put into remission or progression may be halted or slowed. The terms "prevent" and "preventing" mean that a disease, disorder, condition, and/or side effect is avoided altogether or in part.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "administration" (e.g., "administering" a compound) in reference to the ATP analogs, nucleoside analogs, nucleobase analogs, and/or adenosine receptor antagonists of the invention means introducing the ATP analogs, nucleoside analogs, nucleobase analogs, and/or adenosine receptor antagonists into the system of the animal or human in need of treatment. When the ATP analogs, nucleoside analogs, nucleobase analogs, and/or adenosine receptor antagonists of the invention are provided in combination with one or more other active agents (e.g., a cytotoxic agent, etc.), "administration" and its variants are each understood to include concurrent and sequential introduction of the ATP analogs, nucleoside analogs, nucleobase analogs, and/or adenosine receptor antagonists and other agents.

Many ATP analogs, such as TKIs, act by binding to the ATP binding pocket of tyrosine kinases, thereby preventing their phosphorylation and subsequent signaling cascades. Other ATP analogs, such as Bcl-2 inhibitors or PARP inhibitors, act to inhibit Bcl-2 and PARP, respectively. It has now been shown that such ATP analogs have off-target effects. Without wishing to be bound by theory, it is believed that such ATP analogs bind to the ATP pocket of nucleoside and nucleobase transporters. This binding to nucleoside and nucleobase transporters is believed to lead to an accumulation of adenosine in the extracellular environment of the intestinal epithelium, which in turn leads to enhanced stimulation of adenosine receptors and chloride secretion into the intestine, causing diarrhea. Other off-target effects include the binding of ATP analogs to adenosine receptors in the skin. This binding is believed to cause skin toxicity, presenting as hand-foot syndrome, in patients being treated with ATP analogs. Accordingly, it is now shown that the use of an adenosine receptor antagonist can prevent and/or treat ATP analog-induced diarrhea and other side effects such as hand-foot syndrome.

Since the mechanism causing the diarrhea and the hand-foot syndrome and the mechanism of the cytotoxic anticancer effects of the ATP analogs are distinct, it is possible to administer the adenosine receptor antagonist without substantially affecting the cytotoxic anticancer effects of the ATP analogs. For example, TKIs cause diarrhea and hand-foot syndrome through enhanced adenosine receptor stimulation, whereas they exhibit their cytotoxic anticancer effect through inhibition of tyrosine kinase phosphorylation. Use of an adenosine receptor antagonist inhibits adenosine receptor stimulation caused by the TKI without substantially affecting the cytotoxic anticancer activity of the TKI.

Therefore, in another aspect, there is provided a method for preventing and/or treating an ATP analog-induced side effect in a subject, the method comprising administering an effective amount of an adenosine receptor antagonist to the subject.

Additionally, this separation of the mechanisms of the side effects from the therapeutic effects of the ATP analogs allows for maintaining or escalating the dose intensity of the ATP analogs, thereby improving their anticancer effects.

Therefore, in another aspect, there is provided a method for maintaining or escalating dose intensity of an ATP analog in a subject, the method comprising administering the ATP analog with an adenosine receptor antagonist.

In other aspects, it is also now demonstrated that ATP analogs and nucleoside or nucleobase analogs may be administered in combination treatments to prevent and/or treat cancer. It is shown that ATP analogs exhibit off-target effects by binding to and inhibiting nucleoside and nucleobase transporters, therefore preventing efficient uptake of nucleoside or nucleobase analogs into cells. By administering ATP analogs and nucleoside or nucleobase analogs in a specific schedule, with the nucleobase or nucleoside analogs being administered before the ATP analogs, synergy in the prevention and/or treatment of cancer can be observed. Therefore, in another aspect, there is provided a method for treating and/or preventing cancer, wherein the method comprises administering an ATP analog in combination with a nucleoside or nucleobase analog, wherein the nucleoside or nucleobase analog is administered before the ATP analog.

As it has now been shown that ATP analogs, such as TKIs, Bcl-2 inhibitors, and PARP inhibitors, inhibit nucleoside and/or nucleobase transporters, this leads to new treatment modalities for combination treatments with ATP analogs and nucleosides and/or nucleobases. Providing a nucleoside and/or nucleobase analog before the use of an ATP analog will allow the nucleoside and/or nucleobase analog to enter cells and exert a cytotoxic effect before the ATP analog inhibits its transport. The nucleobase, 5-FU, has a short half-life of 20 minutes and is typically administered on days 1 and 2 of a 14 day cycle using the FOLFOX regimen. In certain embodiments, in order to add an ATP analog to the FOLFOX regimen in accordance with the present invention, the ATP analog is administered after administration of the 5-FU is stopped. The ATP analog could be administered immediately following 5-FU or it could be administered, for example, 1-12 hours after stopping 5-FU treatment. There could be some overlap between the treatment with the 5-FU and the ATP analog, however, it will be appreciated that the efficacy of the 5-FU treatment will be better if overlap is reduced or avoided. In another aspect, the ATP analog is administered starting on day 3 of the 14 day cycle. There may be a single treatment with the ATP analog or it may continue for two or more days. In another aspect, the treatment continues until day 10 of a typical FOLFOX regimen.

If a XELOX regimen is being used rather than a FOLFOX regimen, capecitabine is used rather than 5-FU. Capecitabine requires 14 days of treatment in a typical XELOX regimen, therefore, in an embodiment, the ATP analog is administered at least at day 14 of the regimen. In another aspect, the ATP analog would be administered, for example, on day 15 of a XELOX regimen. There could be some overlap between the treatment with capecitabine and the ATP analog, however, it will be appreciated that the efficacy of the capecitabine treatment will be better if overlap is reduced or avoided. Advantageously, ATP analogs such as TKIs tend to work better in combination with older and less expensive regimens that use 5-FU, due to the shorter half-life of 5-FU as compared to capecitabine, which aids in reducing or avoiding any overlap between the use of the nucleoside or nucleobase analog and the ATP analog.

In another aspect, combination treatments are provided that include an ATP analog together with a nucleoside and/or nucleobase analog, as well as an adenosine receptor antagonist, in order to treat and/or alleviate adenosine-mediated side effects of the ATP analog. The nucleoside and/or nucleobase analog is typically administered first so that it can enter the cell and exert an effect. The ATP analog and the adenosine receptor antagonist are then administered, for example. The ATP analog may be administered first in order to determine whether the patient is at risk of ATP analog-induced side effects, such as diarrhea. If no side effects are observed, the adenosine analog may not be necessary. Alternatively, the patient may be administered the ATP analog and the adenosine receptor antagonist simultaneously in order to prophylactically avoid any side effects that may occur. The adenosine receptor antagonist could also be used before the ATP analog in order to ensure that sufficient adenosine receptor antagonism is present before the ATP analog is introduced and thereby prevent onset or reduce severity of an ATP analog-induced side effect.

The ATP analogs, nucleoside analogs, and nucleobase analogs, useful according to the present invention may have an $IC_{50}$ value for a cancer cell population, when administered as single agents, of less than about 1000 nM, typically less than about 800 nM, more typically less than about 500 nM, even more typically less than about 200 nM. When administered in combination treatments, concurrently or sequentially, the $IC_{50}$ value may be synergistically reduced such that their combined effect is greater than the sum of their individual effects. In other aspects, the $IC_{50}$ value may be additively reduced such that their combined effect is approximately equal to the sum of their individual effects. Thus the $IC_{50}$ value for a cancer cell population when ATP analogs, nucleoside analogs, and/or nucleobase analogs are administered in combination may be less than about 500 nM, typically less than about 200 nM, more typically less than about 100 nM, even more typically less than about 75 nM.

The ATP analogs, nucleoside analogs, nucleobase analogs, and adenosine receptor antagonists of this invention may be administered to mammals, typically humans, either alone or, in combination with pharmaceutically acceptable carriers or diluents, optionally with known adjuvants, in a pharmaceutical composition, according to standard pharmaceutical practice. The compounds can be administered orally or parenterally, including the intravenous, intramuscular, intraperitoneal, and subcutaneous routes of administration.

The ATP analogs, nucleoside analogs, nucleobase analogs, and adenosine receptor antagonists of the present invention may also be combined and/or co-administered with other therapeutic agents that are selected for their particular usefulness against the cancer that is being treated. For example, the compounds of the present invention may be combined and/or co-administered with anti-cancer agent(s).

Examples of anti-cancer agents include, without being limited thereto, the following: estrogen receptor modulators, androgen receptor modulators, retinoid receptor modulators, cytotoxic agents, mTOR inhibitors, antiproliferative agents, tyrosine kinase inhibitors, prenyl-protein transferase inhibitors, HMG-CoA reductase inhibitors, HIV protease inhibitors, reverse transcriptase inhibitors, angiogenesis inhibitors and combinations thereof. The present compounds may also be useful with other treatments, such as when co-administered with radiation therapy.

If formulated as a fixed dose, such combination products employ the ATP analogs, nucleoside analogs, nucleobase analogs, and/or adenosine receptor antagonists of this invention within their approved dosage range and the other pharmaceutically active agent(s) within its approved dosage range. The ATP analogs, nucleoside analogs, nucleobase analogs, and adenosine receptor antagonists of the present invention may alternatively be used sequentially with known pharmaceutically acceptable agent(s) when a combination formulation is inappropriate.

When an ATP analog, nucleoside analog, nucleobase analog, and/or adenosine receptor antagonist according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of an ATP analog, nucleoside analog, nucleobase analog, and/or adenosine receptor antagonist is administered to a mammal undergoing treatment for cancer. Administration occurs in an amount from about 0.01 mg/kg of body weight to greater than about 100 mg/kg of body weight per day; from about 0.01 mg/kg of body weight to about 500 mg/kg of body weight per day; from about 0.01 mg/kg of body weight to about 250 mg/kg of body weight per day; or 0.01 mg/kg of body weight to about 100 mg/kg of body weight per day.

Although any combination of doses may be used, typical doses of the ATP analog and the adenosine receptor antagonist, when used in combination, are selected so that the ATP analog achieves the desired effect with respect to treating and/or preventing cancer and so that the adenosine receptor antagonist achieves the desired effect of preventing and/or treating a side effect of the ATP analog, such as diarrhea or hand-foot syndrome. The dose of the adenosine receptor antagonist can be selected so as to reduce the side effect(s), thereby allowing the ATP analog to be used at a specific, desired dosage. Alternatively, the dose of the adenosine receptor antagonist can be selected so as to maintain the side effect(s) to a desired, acceptable level so that the dosage of the ATP analog can be increased.

Similarly, doses of the ATP analog and the nucleoside or nucleobase analog that provide a synergistic effect, greater than additive benefit, or additive benefit, are used. For example, doses of the ATP analog and the nucleoside or nucleobase analog may be selected to lower overall toxicity and side effects while maintaining substantially the same overall treatment effect on cancerous cells as observed when either the ATP analog or the nucleoside or nucleobase analog is administered alone. In another example, doses of the ATP analog or the nucleoside or nucleobase analog may be selected to produce substantially the same overall toxicity and side effects while increasing the treatment effect on cancerous cells as observed when either the ATP analog or nucleoside or nucleobase analog is administered alone.

By administering the ATP analogs and nucleoside and/or nucleobase analogs in combination, one or both of the analogs may be advantageously administered at doses lower than that currently used in conventional cancer treatments, without substantially reducing the efficacy of the cancer treatments. This has the benefit of reducing toxicity of the combination. In addition, the toxicity of the analogs being co-administered may be less due to either a lower required dose or improved toxicological properties; this has the effect of further lowering overall toxicity of the combination without compromising the overall treatment effect.

For example, the analogs can be used together (concurrently or sequentially) in ratios of about 1:99 to about 99:1, about 90:10 to about 10:90, about 25:75 to about 75:25, about 50:50, or any ratio therebetween. When an adenosine receptor antagonist is further used for treatment, it may be included in any suitable ratio with the other two components from about 1:99 to about 99:1, about 90:10 to about 10:90, about 25:75 to about 75:25, about 50:50, or any ratio therebetween. In another aspect, the ATP analog, nucleobase or nucleoside analog, and the adenosine receptor antagonist are used in a ratio of 1:1:1. When the ATP analog and the adenosine receptor antagonist are used together (concurrently or sequentially), they may be used in ratios of about 1:99 to about 99:1, about 90:10 to about 10:90, about 25:75 to about 75:25, about 50:50, or any ratio therebetween.

The use of more than one ATP analog and nucleoside or nucleobase analog at a lower dose than each agent being used alone, includes doses that are, for example, at most about 95%, about 90%, about 85%, about 80%, about 75%, about 60%, about 50%, about 40%, about 30%, about 20%, about 10%, about 5%, about 3%, about 2%, about 1%, about 0.75%, about 0.5%, about 0.25%, or about 0.1%, etc. of the dose of each agent being used alone. At these doses, a synergistic effect in the treatment of cancerous cells may be observed.

It is herein shown that certain TKIs are ATP analogs and exhibit off-target effects by stimulating adenosine receptors. In view of this knowledge provided by the present application, a skilled person could reasonably and soundly predict that the off-target effects of TKIs, such as diarrhea and hand-foot syndrome, are a result of this ATP analog activity. Therefore, it is reasonable to conclude, in view of the teachings found herein, that these off-target effects can be prevented and/or alleviated by co-treatment with ATP receptor antagonists. Similarly, the off-target effects of any other protein inhibitor that acts in the same way by stimulating adenosine receptors, such as certain Bcl-2 inhibitors and PARP inhibitors, can be prevented or alleviated by co-treatment with ATP receptor antagonists.

When introducing elements disclosed herein, the articles "a", "an", "the", and "said" are intended to mean that there are one or more of the elements, except where it is intended to mean that there is one element.

The terms "comprising", "having" and "including", and various endings thereof, are meant to be open ended, including the indicated component but not excluding other elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Figure 2:
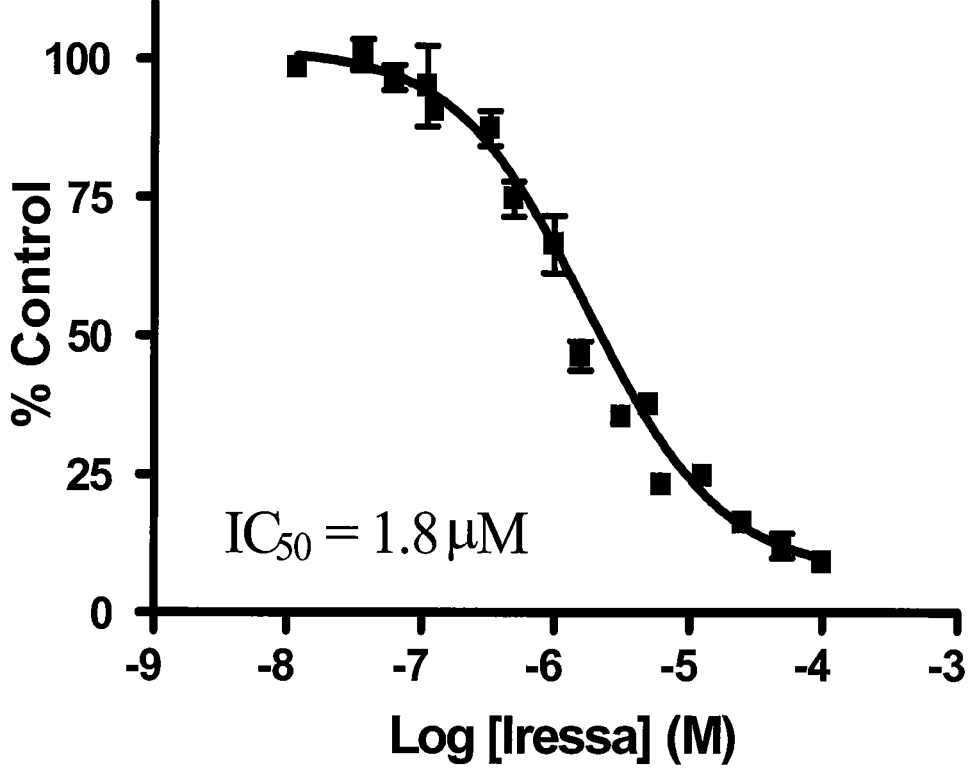
FIG. 2 is a dose response curve showing the inhibition of 1 μM [³H]adenine transport in human renal proximal tubule epithelial cells by gefitinib (Iressa™), averaged across three experiments.
Figure 3:
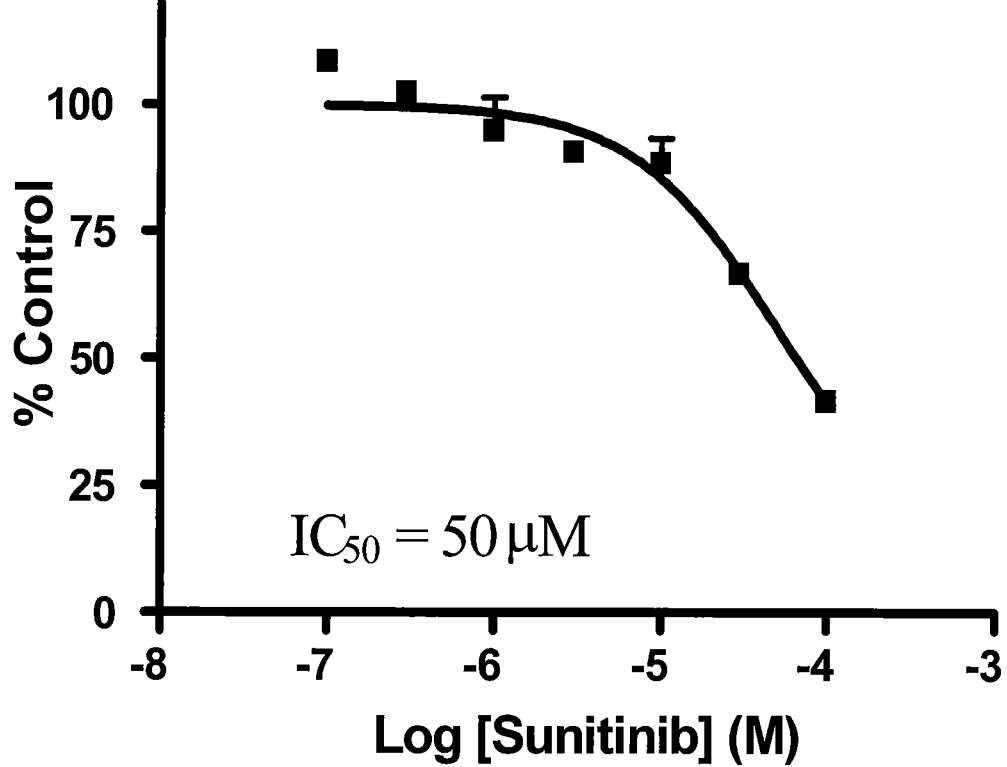
FIG. 3 is a dose response curve showing the inhibition of 1 μM [³H]adenine transport in human renal proximal tubule epithelial cells by sunitinib (Sutent™), averaged across two experiments.

Example 1—Effect of Zactima (Vandetanib), Iressa (Gefitinib) and Sutent (Sunitinib) on Nucleobase Transport Human renal proximal tubule cells (hRPTCs) were seeded in 12-well plates at densities of $10^5$ cells/well and grown for 7 days with medium changes every 3-4 days. On the day of experiments, growth medium was aspirated and cells were washed twice with 1.5 ml of 20 mM Tris-HCl buffer (pH 7.4) containing 150 mM NaCl, 1.2 mM $MgCl_2$ and 1 mM $CaCl_2$ (hereafter referred to as sodium buffer). Inhibition of [$^3$H] adenine transport in hRPTCs by the TKIs vandetanib, gefitinib and sunitinib was investigated by incubating hRPTC cultures with 1 μM [$^3$H]adenine in sodium buffer at pH 7.4 in the absence or presence of graded concentrations of vandetanib, gefitinib and sunitinib. At the end of 2 minute incubations, cells were washed twice with sodium buffer and intracellular accumulation of [$^3$H]adenine was determined by solubilizing cells with 5% Triton-X-100 and subsequent determination of radioactivity in a scintillation counter. Data are presented as percent of values obtained in the absence of a competitor (controls). Resulting concentration-effect curves were analyzed by nonlinear regression analysis using Graph Pad Prism software version 4.0 (Graph Pad Software Inc., San Diego, CA) to obtain $IC_{50}$ values for the compounds. Results are shown in FIGS. 1, 2 and 3.

As can be seen from FIG. 1, vandetanib inhibition of adenine transport was partial and the $IC_{50}$ was found to be at least 100 μM. FIG. 2 shows that the $IC_{50}$ value for gefitinib inhibition of adenine transport was 1.8 μM. FIG. 3 shows that the $IC_{50}$ value for sunitinib inhibition of adenine transport was 50 μM. It is clear from these figures that although vandetanib, gefitinib and sunitinib all inhibit nucleobase transport activity, gefitinib is the most potent inhibitor of the tested adenine nucleobase transporters, thus indicating that, while all ATP analogs tested inhibited nucleobase transport activity, different ATP analogs may inhibit nucleobase transport activity to different extents.

Example 2—FOLFOX Regimen Including a TKI

An exemplary FOLFOX regimen including a TKI such as cediranib is described below:
Day 1:
    Leucovorin 200 mg/m$^2$ (0-2 hrs)
    Oxaliplatin 85 mg/m$^2$ (0-2 hrs)
    5-Fluorouracil (5-FU) 400 mg/m$^2$ (bolus at 2 hrs)
    5-FU 600 mg/m$^2$ (2-22 hrs)
Day 2:
    Leucovorin 200 mg/m$^2$ (0-2 hrs)
    5-FU 400 mg/m$^2$ (bolus at 2 hrs)
    5-FU 600 mg/m$^2$ (2-22 hrs)
Day 3-Day 10:
    TKI such as Cediranib (30 mg/day)
Day 11-14:
    No treatment
Day 15:
    Cycle 2 starts

Example 3—Effects of Adenosine, Adenosine Receptor Antagonists, and TKIs on Human Nucleoside Equilibrative Transporters (hENTS)

Introduction:

T84 cells are used as a model for epithelial chloride ($Cl^-$) secretion (Strohmeier et al., J Biol Chem 1995, 270, 2387). Matthews et al. (Surgery 1994, 116, 150; J Clin Invest 1995, 96, 117) showed that adenosine released from cultured intestinal epithelial cells during hypoxia activates the $Cl^-$ secretion via activation of the adenosine receptors (A2b) (Stehle et al., Mol Endocrinol 1992, 6, 384). Tally et. al, (Surgery 1996, 120, 248) showed that human equilibrative nucleoside transporters (hENTs) localized on intestinal epithelial cells scavenge free adenosine thus regulating the concentrations of adenosine available to interact with adenosine receptors (A2b) localized on intestinal cells leading to activation of $Cl^-$ secretion and adenosine induced diarrheal response.
Methods:

T84 cells were routinely grown in DMEM/F12 (1:1) cell culture media with 10% FBS, 1 mM sodium pyruvate, 1× penicillin/streptomycin and 10 mM HEPES. For experiments described in this report, T84 cells were grown on 12 mm snapwell inserts for 6-8 days with media changes every 2-3 days. Trans epithelial electric resistance (TEER) values were recorded before experiments and were higher than 1000 Ohms/cm2. On the day of the experiment the filters were mounted in Ussing chambers and filled with Ringers solution (Tally et al., Surgery 1996, 120, 248). Compounds were added in small aliquots to the basolateral or apical chamber and the secretory response was measured as an increase in short-circuit current ($I_{SC}$) due to $Cl^-$ secretion and was monitored as a function of time.

In experiments described herein, effects of adenosine and the interaction of the hENT inhibitor nitrobenzylmercaptopurine riboside (NBMPR) were studied to measure secretory response ($I_{SC}$) as a result of addition of extracellular adenosine or blocking adenosine scavenging by inhibitors of hENTs. These induced increases in $I_{SC}$ could be abolished by adding antagonists/inhibitors of adenosine receptors such as 8-phenyltheophylline (8-PT) (Tally et al., Surgery 1996, 120, 248). The inhibitory effect of theophylline, an analogue of 8-PT, on adenosine induced currents in T84 cells was also studied.

It is also shown that some tyrosine kinase inhibitors (TKIs), inhibited the activity of hENTs on intestinal epithelial cells resulting in localized higher concentrations of adenosine to interact with the adenosine receptors thus causing activation and secretory response.

Figure 4:
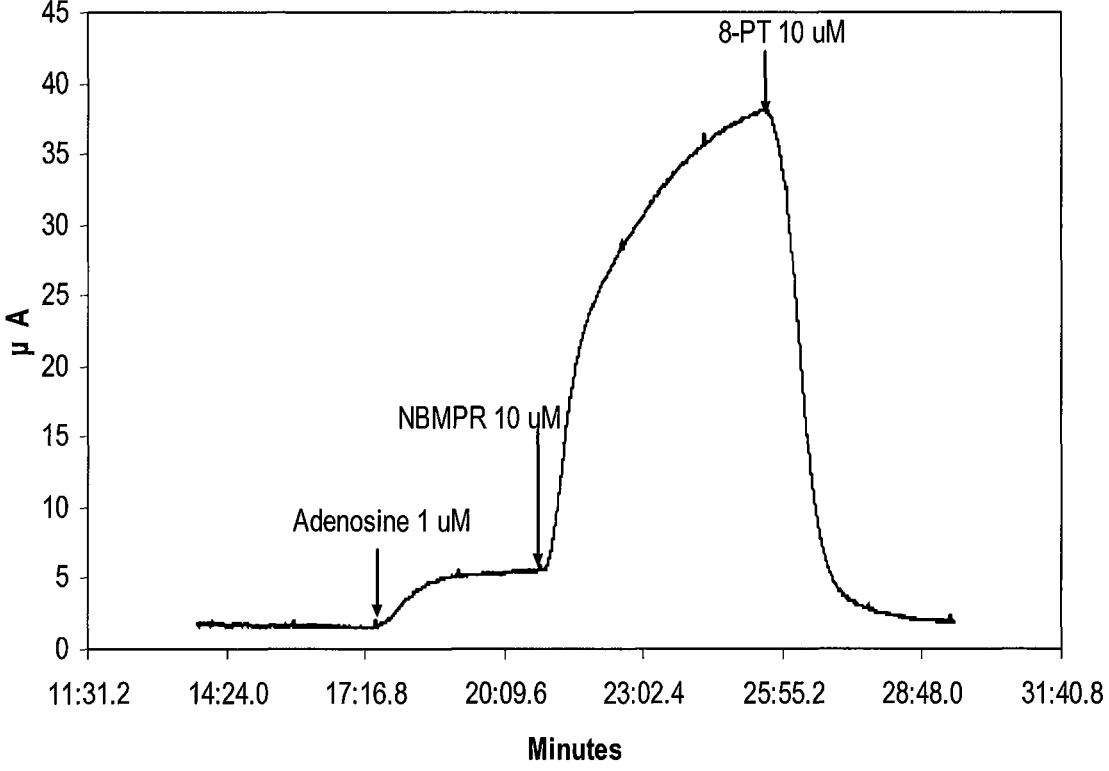
FIG. 4 shows that adenosine (Ado) and nitrobenzylmercaptopurine riboside (NBMPR) induced currents in T84 cells and that this was inhibited by 8-phenyltheophylline (8-PT)

Results:

FIG. 4 shows the effect of addition of 1 μM adenosine to the basolateral side of the membrane. After monitoring the $I_{SC}$ for a few minutes, 10 μM NBMPR (an inhibitor of hENTs) was added to the same side. Blockade of hENTs by NBMPR, a high affinity inhibitor, resulted in much higher $I_{SC}$ due to inhibition of adenosine transport via hENTs. Addition of 10 μM 8-PT, a high affinity inhibitor of adenosine receptors blocked further increase in $I_{SC}$ and the $I_{SC}$ returned to baseline levels. This result clearly suggests that adenosine-induced secretory currents are increased substantially by inhibition of hENT activity. This could be due to increase in localized adenosine concentrations leading to activation of adenosine receptors as shown by Tally et. al (Surgery 1996, 120, 248).

Figure 5:
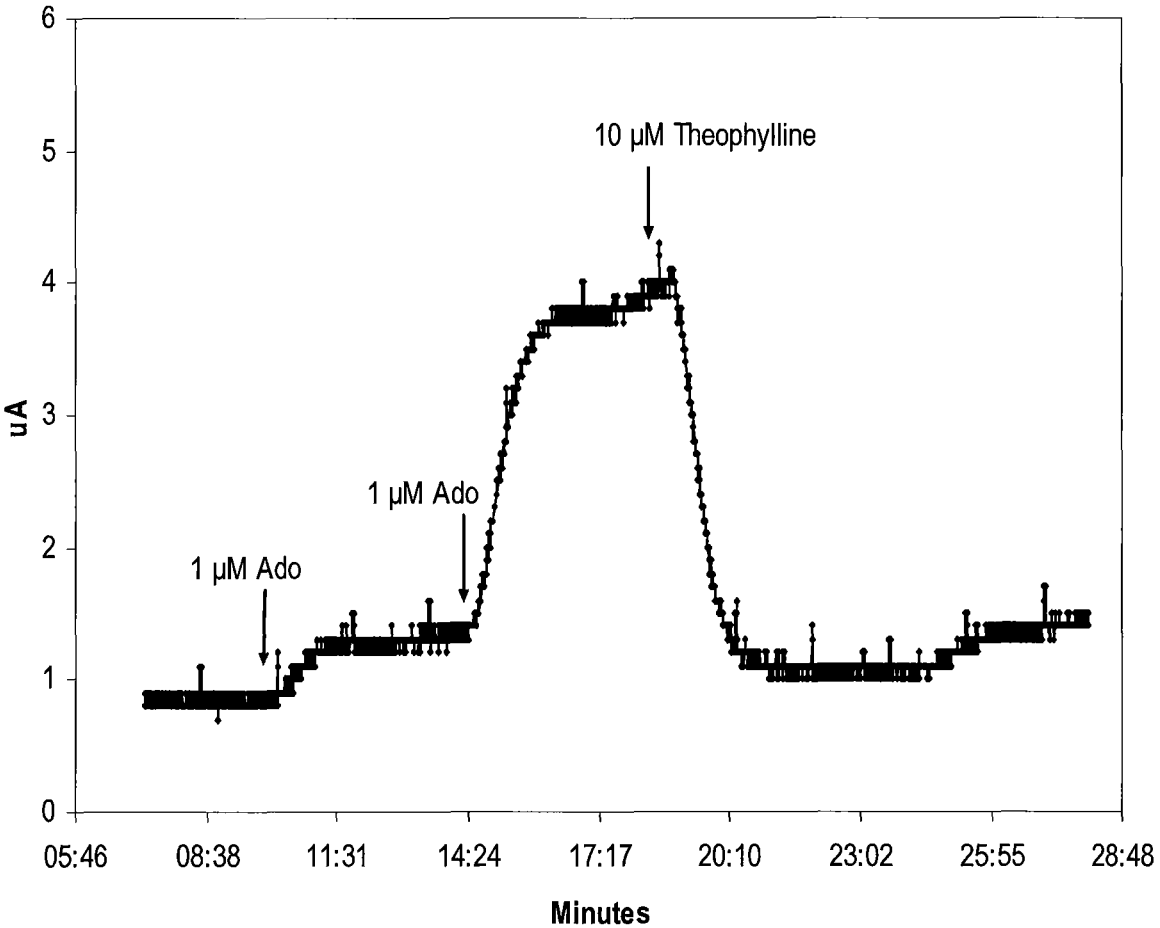
FIG. 5 shows the effect of theophylline on adenosine induced currents in T84 cells.

In FIG. 5, an adenosine induced increase in $I_{SC}$ was also blocked by the addition of 10 μM theophylline, an antagonist of adenosine receptors.

Figure 6:
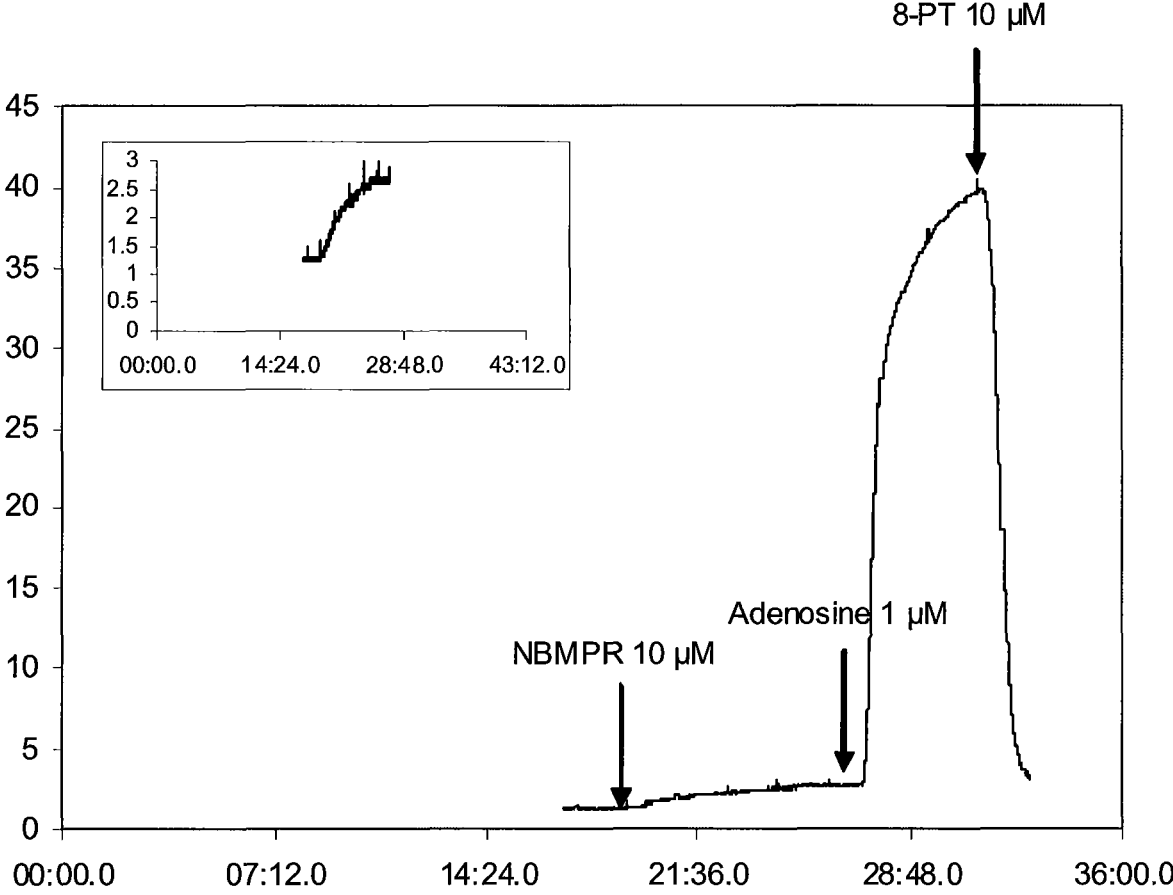
FIG. 6 shows the potentiation of adenosine induced currents by pretreatment with the human equilibrative nucleoside transporter (hENT) inhibitor NBMPR in T84 cells and that this was inhibited by 8-PT.

The effect of 10 μM NBMPR added basolaterally, (FIG. 6) was used to evaluate the inhibition of the adenosine transporter (hENTs) scavenging function of the epithelial cells without the addition of extracellular adenosine. The increase in $I_{SC}$ was monitored for few minutes and there was a steady increase in $I_{SC}$ with time (inset of FIG. 6) thus suggesting possible accumulation of endogenous adenosine in the extracellular medium due to blockade of adenosine transporter (hENTs) function. This hypothesis was further tested by adding 1 μM adenosine to the basolateral side. A substantial increase in $I_{SC}$ was observed almost instantaneously and the observed increase in $I_{SC}$ caused by 1 μM adenosine was much higher than observed in FIGS. 4 and 5 in the absence of the hENT inhibitor but similar to the levels observed after addition of NBMPR in FIG. 4, thus indicating that inhibition of hENTs would cause accumulation of adenosine leading to activation of adenosine receptors. Addition of 8-PT reversed the increase in $I_{SC}$ to baseline activity.

Figure 7:
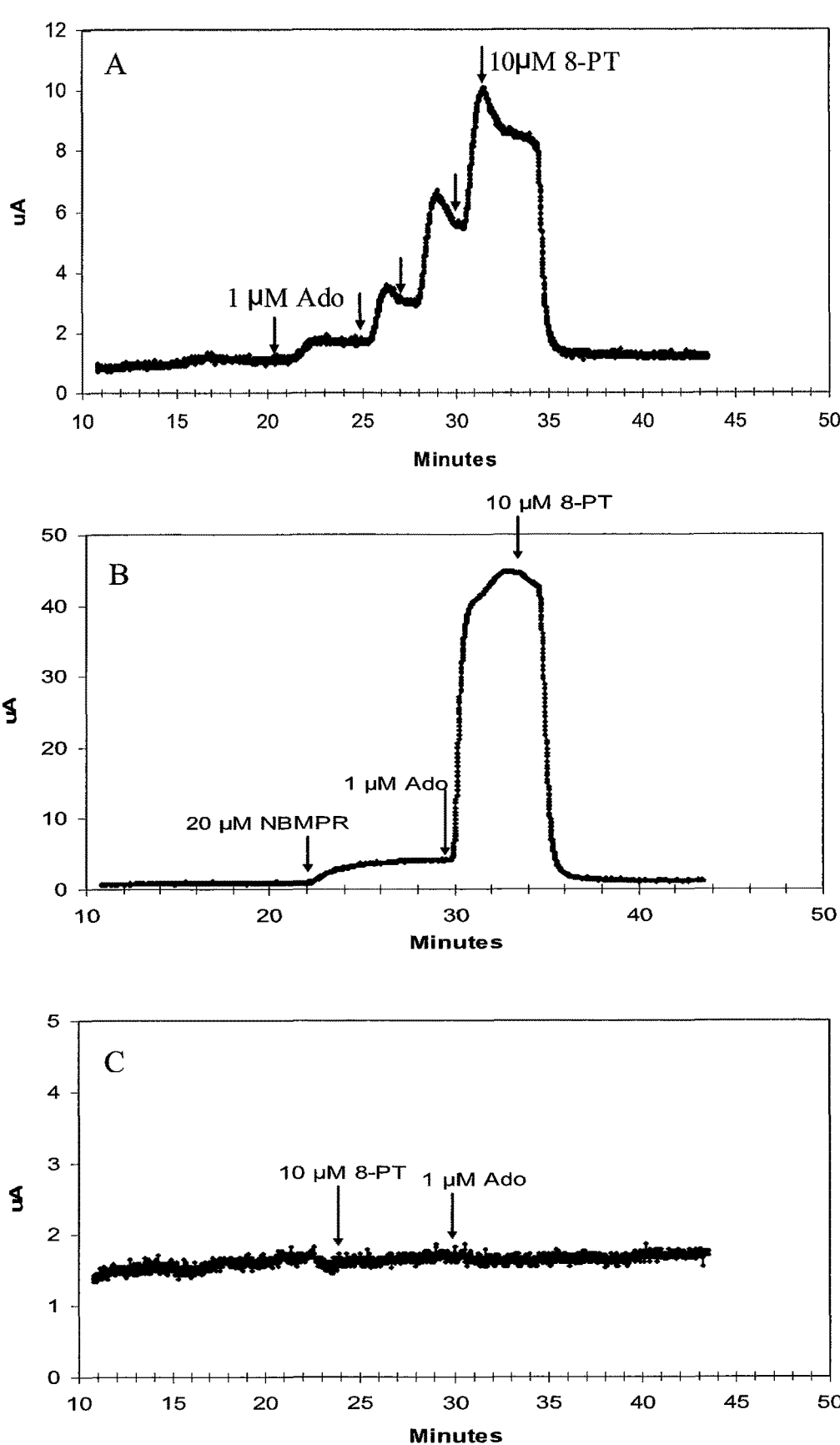
FIG. 7 shows the characterization of adenosine effects in T84 cells and the inhibition of adenosine induced currents by pretreatment with 8-PT.

In FIG. 7, the effect of increasing concentrations of adenosine added basolaterally (in 1 μM increments) on the increase of $I_{SC}$ in T84 cells (panel A) was tested. With each successive addition of adenosine, $I_{SC}$ increased. The effect of basolateral addition of 20 μM NBMPR on induction of currents in T84 cells was retested. Induction of currents were observed which could be due to inhibition of mediated flux of adenosine via hENTs (panel B) leading to accumulation of adenosine on the basolateral surface and leading to activation of adenosine receptors. Addition of 10 μM 8-PT to the basolateral membrane prior to addition of 1 μM adenosine to the basolateral side (panel C) showed no induction of $I_{SC}$ in T84 cells thus showing that blockade of adenosine receptors by antagonists led to inhibition of activation by adenosine.

These results thus far suggest that inhibitors of hENTs could lead to inhibition of adenosine transport activity on the basolateral membrane of T84 cells and could potentially enhance the concentration of adenosine around the vicinity of adenosine receptors leading to activation of adenosine receptors and subsequent induction of chloride secretory currents. It has been shown that the adenosine receptor antagonists 8-PT and theophylline block the induction of currents, possibly due to blockade of adenosine receptor activation. Other results have identified that most TKIs inhibit hENT activity, some more potently than others (data not shown). It was therefore hypothesized that the unwanted side effects such as diarrhea, of some TKIs could possibly be due to inhibition of hENTs by TKIs, leading to accumulation of adenosine and causing activation of adenosine receptors leading to chloride secretory currents. To investigate this, the effect of three TKIs, erlotinib, gefitinib and imatinib was evaluated in experiments similar to those conducted with NBMPR in the T84 model system.

Figure 8:
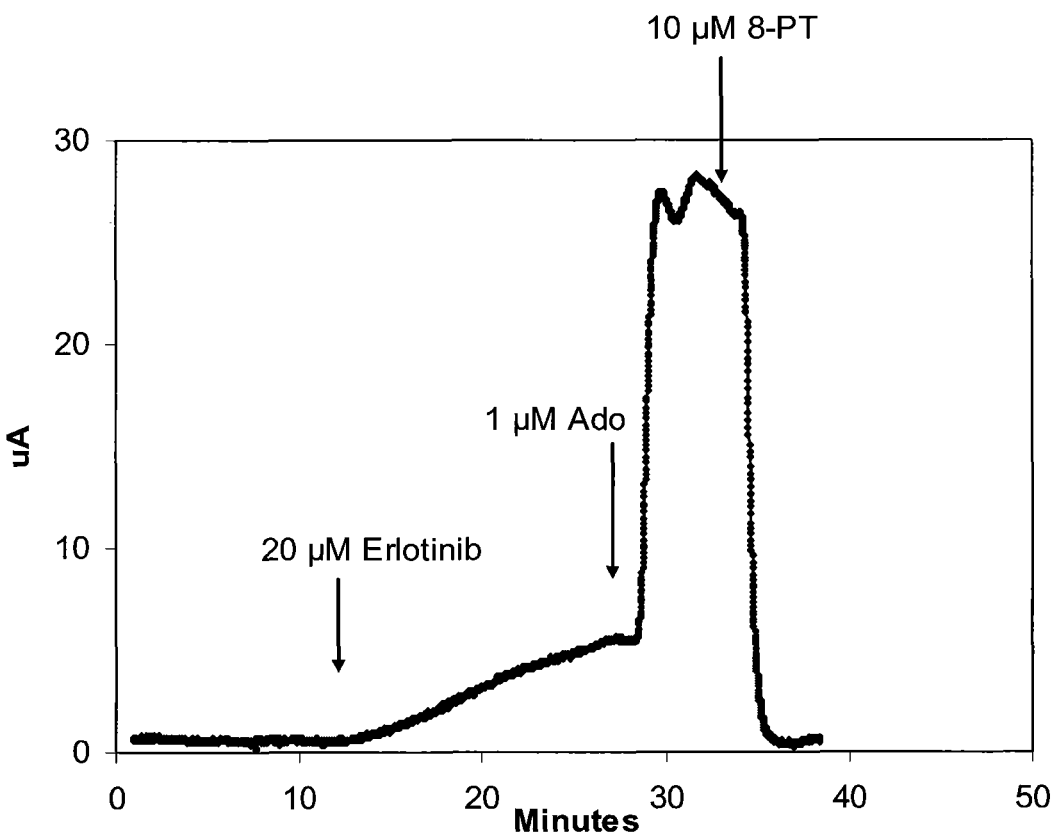
FIG. 8 shows the potentiation of erlotinib induced currents by adenosine in T84 cells and that this was inhibited by 8-PT.

FIG. 8 shows the effect of addition of 20 μM erlotinib to the basolateral side followed by the addition of 1 μM adenosine and later followed by 10 μM 8-PT. Erlotinib caused an increase in $I_{SC}$ similar to that of NBMPR and further additions of adenosine caused a substantial induction of currents as seen with NBMPR and adenosine. These currents were abolished by 8-PT thus suggesting that activation of adenosine receptor is probably responsible for the observed currents.

Figure 9:
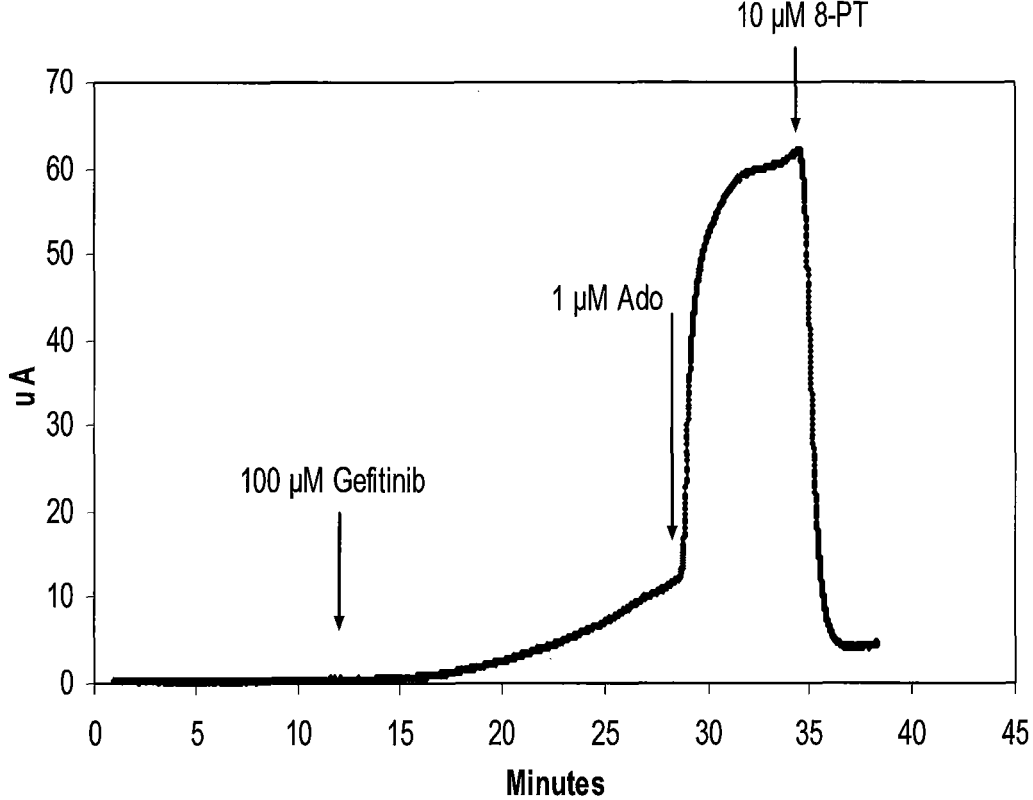
FIG. 9 shows the potentiation of gefitinib induced currents by adenosine in T84 cells and that this was inhibited by 8-PT.

In FIG. 9, the effect of basolateral addition of 100 μM gefitinib to T84 cells, followed by the addition of 1 μM adenosine to the same side is shown. This was later followed by addition of 10 μM 8-PT to the basolateral chamber. Gefitinib caused a slow but steady increase in $I_{SC}$ similar to that of NBMPR and further additions of adenosine caused a substantial induction of currents as seen with NBMPR and adenosine. These currents were abolished by 8-PT thus suggesting that activation of adenosine receptor is probably responsible for the observed currents.

Figure 10:
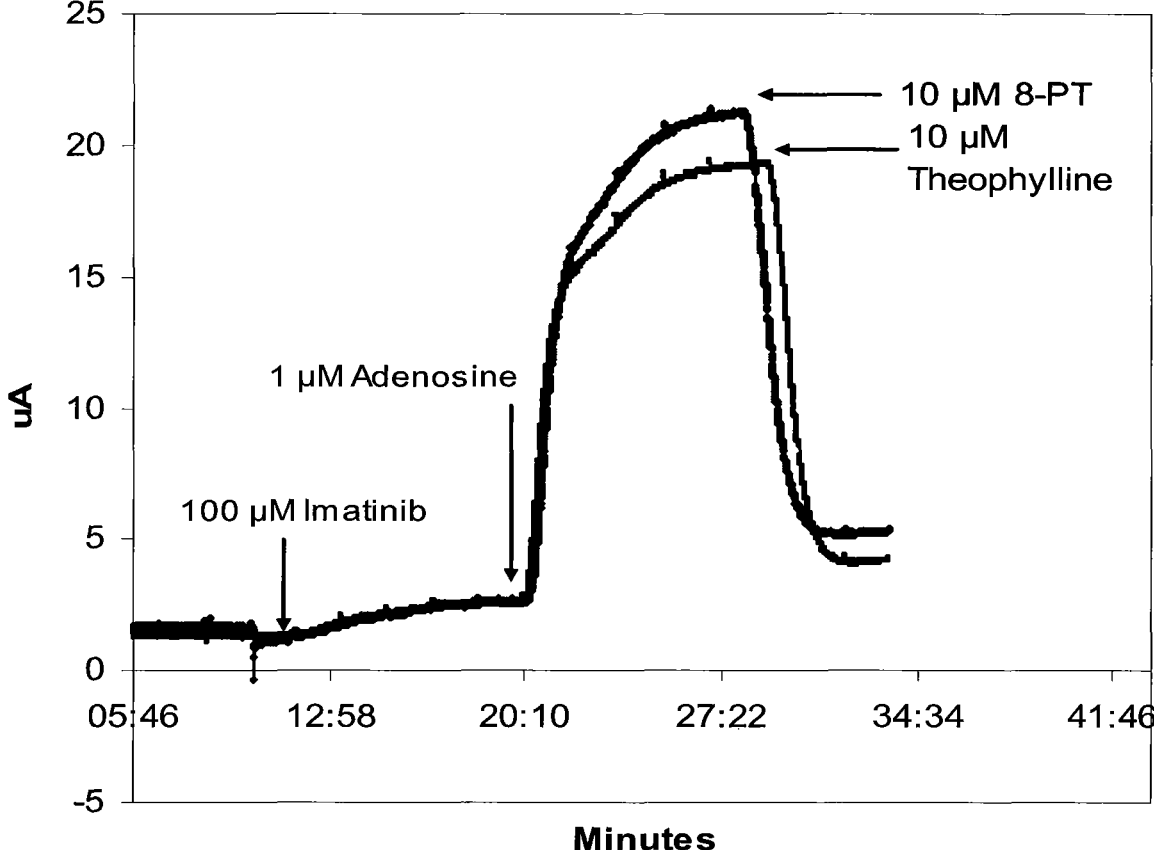
FIG. 10 shows the potentiation of imatinib induced currents by adenosine in T84 cells and that this was inhibited by 8-PT and theophylline.

In FIG. 10, the effect of basolateral addition of 100 μM imatinib to T84 cells, followed by the addition of 1 μM adenosine to the same side is shown. This was later followed by addition of 10 μM 8-PT or 10 μM theophylline to the basolateral chamber. Imatinib caused an increase in $I_{SC}$ similar to that of NBMPR, erlotinib and gefitinib. Further additions of 1 μM adenosine caused a substantial induction of currents as seen with NBMPR, erlotinib and gefitinib. These currents were abolished by 8-PT as well as theophylline thus suggesting that activation of adenosine receptors is likely responsible for the observed currents.

Figure 11:
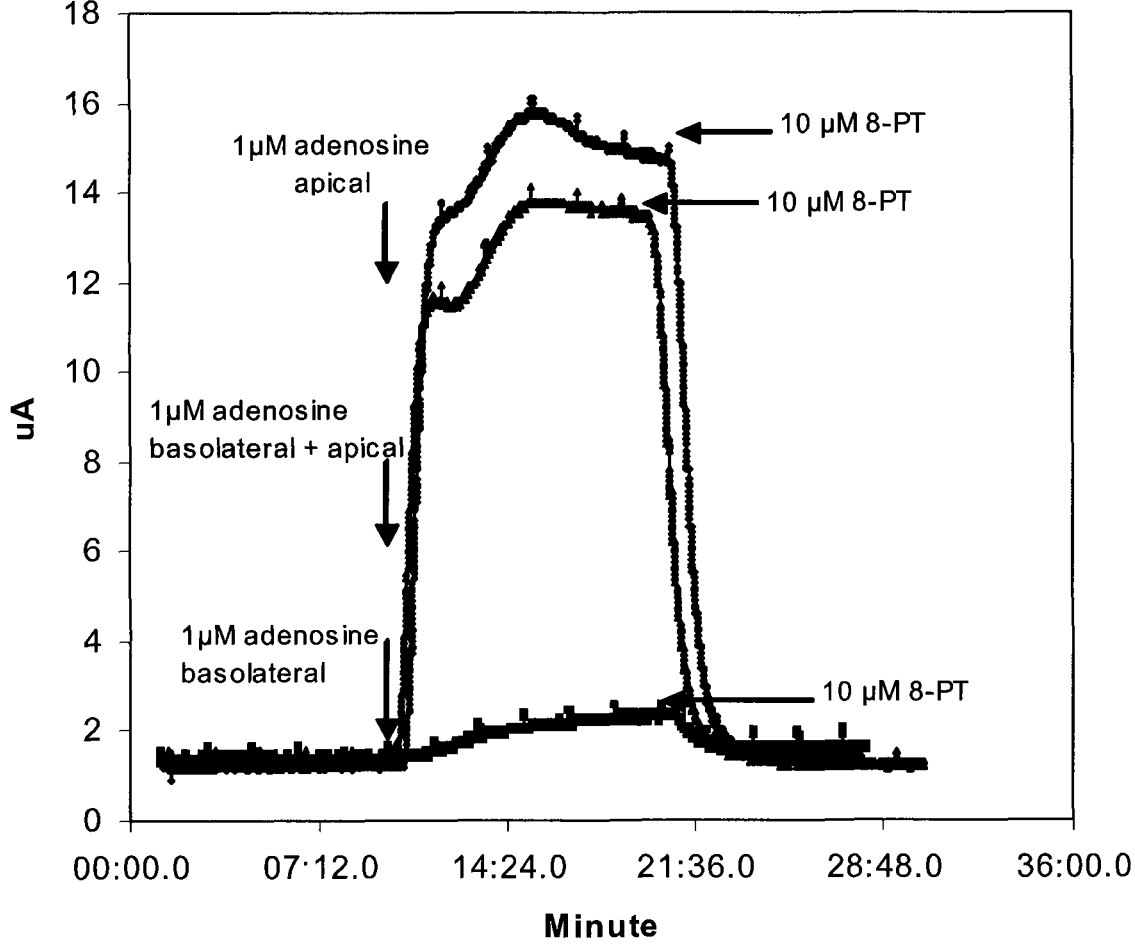
FIG. 11 shows the effect of basolateral or apical or both basolateral and apical addition of 1 μM adenosine in T84 cells and that this was inhibited by 8-PT.

Since intestinal epithelial cells are exposed to orally administered drugs first on the apical (mucosal) side and after absorption of the drugs to the basolateral (serosal side), adenosine effects on different sides of the T84 cell membrane were studied in Ussing chambers. The effect of addition of 1 μM adenosine to basolateral or apical or both sides was studied in induction currents in T84 cells. Addition of adenosine to apical and both sides produced much higher currents than on the basolateral side alone (FIG. 11).

Figure 12:
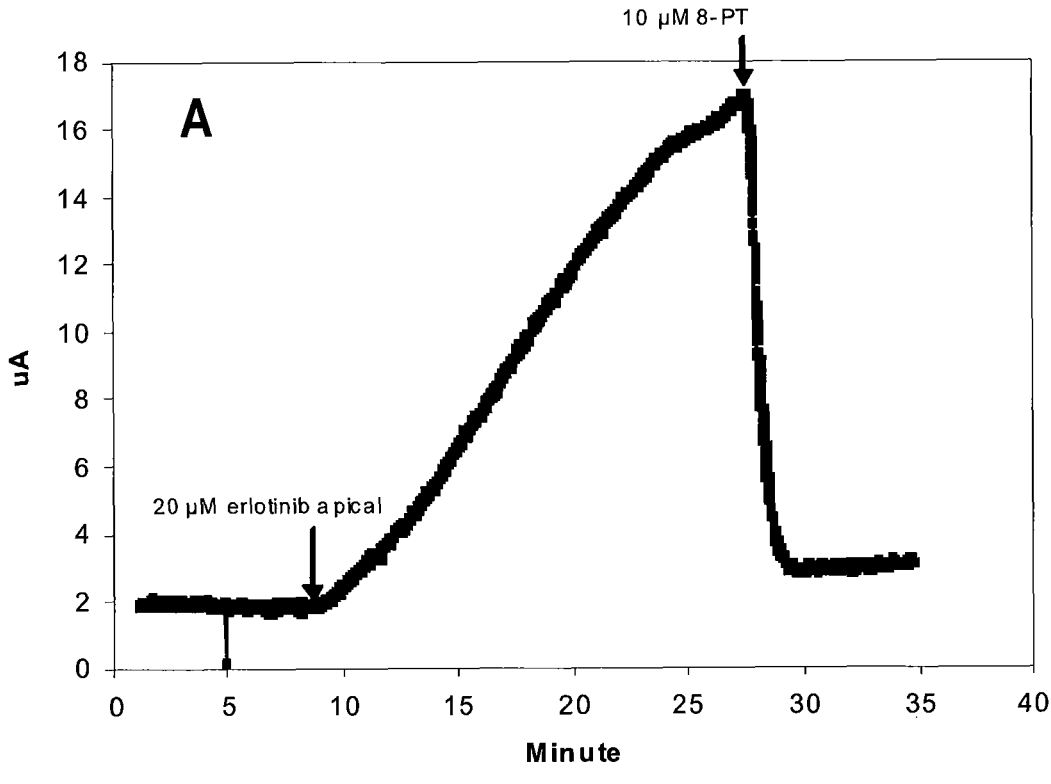
FIG. 12 shows the effect of apical addition of 20 μM erlotinib or 100 μM gefitinib in T84 cells and that this was inhibited by 8-PT.
Figure 12:
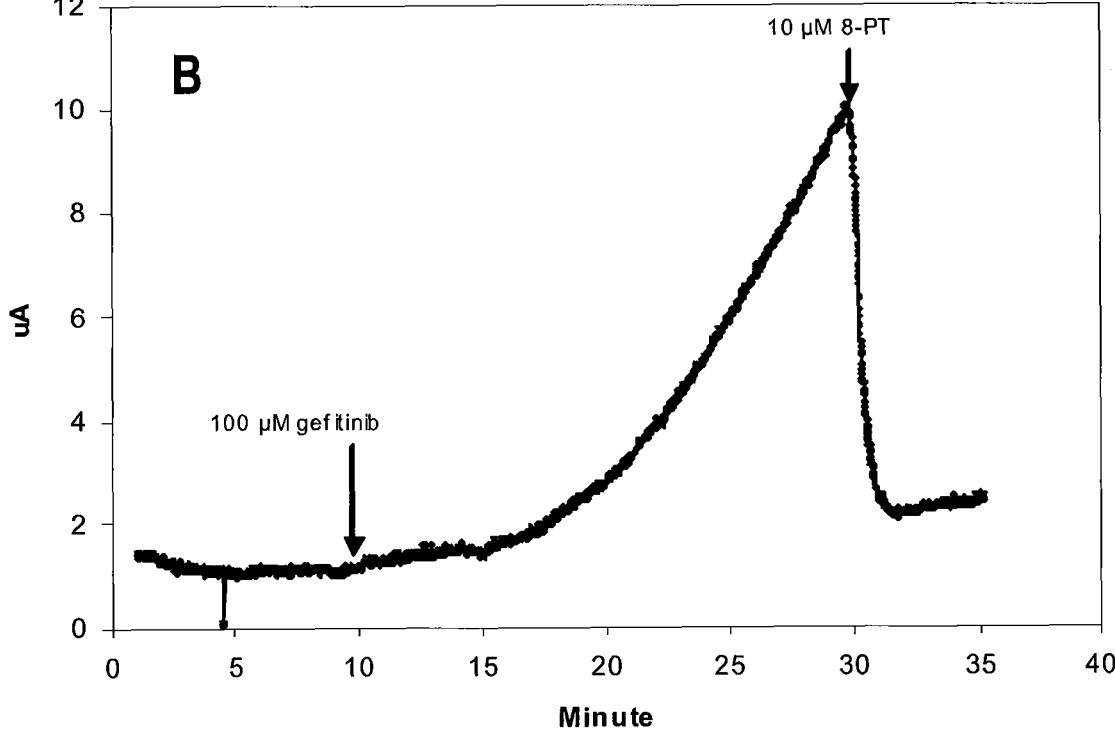

FIG. 12 shows the effect of apical addition of 20 μM erlotinib (panel A) or 100 μM gefitinib (panel B) on induction of currents in T84 cells. The slow increase in currents induced by both erlotinib and gefitinib were abolished by the addition of 10 μM 8-PT to apical side thus suggesting the role of adenosine receptor in activation of currents.

These results support the hypothesis that TKIs inhibit hENTs and could cause accumulation of adenosine, which leads to adenosine receptor activation with subsequent secretory currents. It was also shown that treatment with the adenosine receptor antagonists 8-phenyl-theophylline and theophylline abolished the induction of currents, probably due to inhibition of adenosine receptors. Therefore, it is reasonable to conclude that adenosine receptor antagonists have a role in reducing the diarrheal side effects of TKIs in the clinic.

In view of this data presented with respect to TKIs, it is reasonable to conclude that other protein inhibitors that are also ATP analogs would act in the same way. Since certain TKIs are ATP analogs and exhibit off-target effects by stimulating adenosine receptors, these off-target effects can be prevented and/or alleviated by co-treatment with ATP receptor antagonists. Similarly, the off-target effects of any other protein inhibitor that acts in the same way by stimulating adenosine receptors, such as certain mTOR inhibitors, Bcl-2 inhibitors, and PARP inhibitors, can be prevented or alleviated by co-treatment with ATP receptor antagonists.

Although embodiments have been described above with reference to the accompanying drawings, those of skill in the art will appreciate that variations and modifications may be made without departing from the spirit and scope thereof as defined by the appended claims.

What is claimed is:

1. A method for treating an ATP analog-induced side effect in a subject being treated for cancer, the method comprising administering an effective amount of an adenosine receptor antagonist to the subject, wherein the adenosine receptor antagonist is theophylline, aminophylline, 8-phenyltheophylline or combinations thereof, wherein the ATP analog is a tyrosine kinase inhibitor, the subject is being treated for cancer with the tyrosine kinase inhibitor, and wherein the tyrosine kinase inhibitor causes cytotoxic anticancer effect by inhibiting tyrosine kinase phosphorylation and wherein administering the effective amount of the adenosine receptor antagonist does not substantially affect the cytotoxic anticancer effect of the tyrosine kinase inhibitor;

wherein the side effect is secretory diarrhea associated with activation of adenosine receptors by an accumulation of adenosine caused by inhibition of human equilibrative nucleoside transporters (hENTs) by the tyrosine kinase inhibitor and/or hand-foot syndrome associated with activation of adenosine receptors by an accumulation of adenosine caused by inhibition of human equilibrative nucleoside transporters (hENTs) by the tyrosine kinase inhibitor.

2. The method of claim 1, wherein the tyrosine kinase inhibitor is selected from the group consisting of axtinib, bosutinib, brivanib, cediranib, dasatinib, erlotinib, gefitinib, imatinib, lapatinib, lestaurtinib, nilotinib, pazopanib, semaxanib, sorafenib, sunitinib, vandetanib, vatalanib and combinations thereof.

3. The method of claim 2, wherein the tyrosine kinase inhibitor is gefitinib.

4. The method of claim 1, wherein the adenosine receptor antagonist is specific for the adenosine $A_{2B}$ receptor.

5. The method of claim 1, wherein the adenosine receptor antagonist is theophylline.

6. The method of claim 1, wherein the ATP analog is administered before the adenosine receptor antagonist.

7. The method of claim 1, wherein the adenosine receptor antagonist is administered before the ATP analog.

8. The method of claim 1, wherein the side effect is diarrhea and the method reduces the incidence or severity of the diarrhea.

9. The method of claim 1, wherein the adenosine receptor antagonist is caffeine and the effective amount is from about 0.01 mg/kg to about 30 mg/kg of body weight per day.

10. The method of claim 1, wherein the adenosine receptor antagonist is theophylline or 8-phenyltheophylline and the effective amount is less than 7 mg/kg of body weight per day.

11. The method of claim 1, wherein the adenosine receptor antagonist is theophylline or 8-phenyltheophylline and the effective amount is sufficient to reach a concentration of 10 μM in the extracellular environment of the intestinal epithelium.

12. The method of claim 1, wherein the tyrosine kinase inhibitor and the adenosine receptor antagonist are orally administered.

13. A method for treating secretory diarrhea in a subject being treated with a tyrosine kinase inhibitor in an amount effective to treat cancer and to inhibit human equilibrative nucleoside transporters (hENTs) and cause activation of adenosine receptors by an accumulation of adenosine, the activation of the adenosine receptors causing the secretory diarrhea as a side effect; the method comprising administering an adenosine receptor antagonist in an amount effective to block adenosine receptors and thereby treat the secretory diarrhea, wherein the adenosine receptor antagonist is theophylline, aminophylline, 8-phenyltheophylline or combinations thereof; wherein the tyrosine kinase inhibitor causes cytotoxic anticancer effect by inhibiting tyrosine kinase phosphorylation and wherein administering the adenosine receptor antagonist does not substantially affect the cytotoxic anticancer effect of the tyrosine kinase inhibitor.

14. The method of claim 13, wherein the adenosine receptor antagonist is theophylline or 8-phenyltheophylline and the effective amount is less than 7 mg/kg of body weight per day.

15. The method of claim 13, wherein the adenosine receptor antagonist is theophylline or 8-phenyltheophylline and the effective amount is sufficient to reach a concentration of 10 μM in the extracellular environment of the intestinal epithelium.

16. The method according to claim 13 further comprising maintaining or increasing the dose of the tyrosine kinase inhibitor administered to the subject.

17. The method of claim 13, wherein the tyrosine kinase inhibitor and the adenosine receptor antagonist are orally administered.

* * * * *